US008287445B2

(12) United States Patent
Bailey

(10) Patent No.: US 8,287,445 B2
(45) Date of Patent: Oct. 16, 2012

(54) APPARATUS FOR RECEIVING A PHALLUS

(75) Inventor: Colin Bailey, London (GB)

(73) Assignee: Colin Bailey, London (GB)

( * ) Notice: Subject to any disclaimer, the term of this patent is extended or adjusted under 35 U.S.C. 154(b) by 1225 days.

(21) Appl. No.: 11/991,882

(22) PCT Filed: Sep. 8, 2006

(86) PCT No.: PCT/GB2006/003350

§ 371 (c)(1),
(2), (4) Date: Mar. 10, 2008

(87) PCT Pub. No.: WO2007/029024

PCT Pub. Date: Mar. 15, 2007

(65) Prior Publication Data

US 2009/0149701 A1 Jun. 11, 2009

(30) Foreign Application Priority Data

Sep. 9, 2005 (GB) .................................. 0518464.3

(51) Int. Cl.
*A61F 5/00* (2006.01)

(52) U.S. Cl. ......................................................... 600/38

(58) Field of Classification Search .............. 600/38–41; 128/834, 837; 606/192–193
See application file for complete search history.

(56) References Cited

U.S. PATENT DOCUMENTS

| | | | | | |
|---|---|---|---|---|---|
| 4,022,213 | A | * | 5/1977 | Stein | 604/350 |
| 4,964,416 | A | * | 10/1990 | Foldesy et al. | 128/842 |
| 5,112,324 | A | | 5/1992 | Wallace | |
| 5,458,559 | A | * | 10/1995 | Gauntlett | 600/38 |
| 5,466,235 | A | * | 11/1995 | Shubin, Sr. | 600/38 |
| 5,538,584 | A | | 7/1996 | Metz | |
| 5,628,329 | A | * | 5/1997 | Bennett et al. | 128/842 |
| 6,113,532 | A | * | 9/2000 | Yap | 600/38 |

FOREIGN PATENT DOCUMENTS

| | | |
|---|---|---|
| EP | 0832635 | 4/1998 |
| GB | 2271511 | 4/1994 |

* cited by examiner

*Primary Examiner* — John Lacyk
(74) *Attorney, Agent, or Firm* — Iandiorio Teska & Coleman, LLP

(57) ABSTRACT

Apparatus (2) for receiving a phallus (4), which apparatus (2), comprises a frame (6), a diaphragm (8) supported by the frame (6), and an aperture (10) in the diaphragm (8), the apparatus (2) being such that: (i) the diaphragm (8) is made of a stretchable material; (ii) the stretchable material is such that the aperture (10) is stretchable radially to enable the phallus (4) to extend through the diaphragm (8), the diaphragm (8) is stretchable transversely to extend along the phallus (4) but only for a short length substantially less than the length of the phallus (4), the part of the diaphragm (8) in contact with the phallus (4) acts with a compressible force sufficient to provide the phallus (4) with sexual stimulation, and the diaphragm (8) returns to its original shape after use; and the diaphragm (8) is substantially flat when not in use.

16 Claims, 8 Drawing Sheets

APPARATUS FOR RECEIVING A PHALLUS

FIELD OF THE INVENTION

This invention relates to apparatus for receiving a phallus and, more especially, this invention relates to apparatus for receiving a phallus for the purpose of stimulating the phallus.

DESCRIPTION OF RELATED PRIOR ART

Apparatus for receiving a phallus for stimulatory purposes is well known. The known apparatus is usually tubular, and the tube is often closed at one end. This makes the known apparatus difficult to clean. Difficulty in cleaning can lead to the apparatus becoming unhygienic for use. In addition, the known types of apparatus with their tubular designs are often bulky and/or of an indiscreet appearance.

BRIEF SUMMARY OF THE INVENTION

It is an aim of the present invention to reduce the above mentioned problems.

Accordingly, the present invention provides apparatus for receiving a phallus, which apparatus comprises a frame, a diaphragm supported by the frame, and an aperture in the diaphragm, the apparatus being such that:

(i) the diaphragm is made of a stretchable material;

(ii) the diaphragm is substantially flat when not in use; and characterised in that:

(iii) the stretchable material is such that the aperture is stretchable radially to enable the phallus to extend through the diaphragm, the diaphragm is stretchable transversely to extend along the phallus but only for a short length which is substantially less than the length of the phallus, the part of the diaphragm in contact with the phallus acts with a compressible force sufficient to provide the phallus with sexual stimulation, and the diaphragm returns to its original shape after use; and (iv) the frame supports the diaphragm such that when the phallus extends through the diaphragm then the phallus extends transversely through the frame and projects beyond the frame.

The apparatus of the present invention is essentially the very opposite in concept from the above mentioned known apparatus. More specifically, whilst the known apparatus is tubular in design and therefore long and bulky, the apparatus of the present invention is able to be flat and compact. The use of the diaphragm ensures that the operative part of the apparatus is easily able to be cleaned, and therefore does not suffer from the problem of becoming unhygienic due to poor cleaning. Still further, the use of the diaphragm enables the operative part of the apparatus to be considerably less bulky than a tube, and thus the apparatus of the present invention is able to be produced with a much more discreet appearance than the above mentioned known apparatus.

The apparatus may be one in which the stretchable material is a rubber material, a plastics material, or a rubber-like material. The plastics material may be a thermoplastics material. The stretchable material may be a silicon material. Examples of typical materials that may be used for the stretchable material are fluorosilicon rubber, silicon rubber, silicon sponge, polymer gel, thermoplastic elastomers, thermoplastic rubbers, polyurethane, sorbothane, thermo-set silicon gel, latex, EPDM, silicon, fluorosilicon, neoprene, nitrile and viton rubbers, and styrene ethylene butadiene styrene.

The stretchable material may have a Shore hardness of 1-35.

The stretchable material may be such that during use, it stretches 5-70 mm along the phallus. The length of the stretch of the stretchable material may vary in dependence upon the actual material being used, the thickness of the material being used, and the diameter of the material being used. As indicated above, the degree of stretch of the stretchable material is to be such as to enable the aperture and the stretchable material to accommodate a short length of the phallus, and also to be such that the stretched material grips the accommodated part of the phallus with a sufficient compressive force to provide the phallus with the sexual stimulation.

The stretchable material may be plain. Alternatively, the stretchable material may have a raised pattern. The raised pattern may be in the form of a pattern of circles or dots. Any suitable and appropriate type of raised pattern may be employed.

The stretchable material may be lubricated or not lubricated. When the stretchable material is lubricated, the lubricant may be applied by a user before each use of the apparatus or, alternatively, the stretchable material may be pre-lubricated at the time of manufacture of the apparatus. If desired, lubricant could be applied from applicator means forming part of the apparatus, for example a squeezable pad containing lubricant and which excretes lubricant direct onto the stretchable material.

The frame is preferably a laminated frame. Other types of frame may be employed so that, for example, the frame may be a single layer frame.

The diaphragm is able to be held between first and second layers of the frame. The diaphragm may be held in position between the first and second layers of the frame with an adhesive, or with any other suitable and appropriate fixing means. In all embodiments of the invention, the diaphragm may alternatively be moulded to be integral with the frame.

Usually, the frame will be a rigid frame. If the frame is other than a rigid frame, then the frame has to be sufficiently strong as to be able to hold the diaphragm and enable the diaphragm to stretch as indicated above during use of the apparatus.

Usually, the apparatus will be one in which the frame defines a circular area, and in which the circular area is filled by the diaphragm. The area may be other than circular if desired. The circular area may be 30-100 mm in diameter, and is preferably 60 mm in diameter.

The aperture in the diaphragm may be a circular aperture. Alternatively, the aperture in the diaphragm may be a three-legged aperture. The aperture may be of 1-60 mm in diameter. Preferably the aperture is 20 mm in diameter. The aperture may also be formed by one or more slits. Generally, the aperture in the diaphragm may be of any desired and suitable shape and size.

The apparatus may include a handle portion. The handle portion may be a dedicated handle portion.

Alternatively, the handle portion may form a part of the apparatus which serves a purpose in addition to being a handle portion. In this case, the handle portion may form part of a connecting portion which connects the frame, the diaphragm and the aperture to at least one other frame, diaphragm and aperture. Thus, for example, the handle portion may form part of a connecting portion which connects the frame, the diaphragm and the aperture to two or three other units each comprising a frame, diaphragm and aperture. In this case, the design of the different sets of the frame, diaphragm and aperture may be the same or they may be different. For example, different diaphragms and/or different apertures may be employed to give different stimulatory effects.

Preferably, the apparatus is one in which the frame and the diaphragm are substantially flat when the apparatus is not in use.

If desired, the entire apparatus may be substantially flat when not in use.

Alternatively, the apparatus may be one in which the entire apparatus is not substantially flat when not in use, and in which the part of the apparatus which serves a purpose in addition to being a handle portion is a vibration unit. Alternatively, the apparatus may be one in which the entire apparatus is not substantially flat when not in use, and in which there are two sets of the frame, diaphragm and aperture, and in which the apparatus is twisted such that it curves in more than one plane.

Alternatively, the apparatus may be one in which the entire apparatus is not substantially flat when not in use, in which there are at least two sets of the frame, diaphragm and aperture, and in which the apparatus is formed such that the diaphragms and their apertures are in line. In this case, there may be two sets of the frame, diaphragm and aperture, or there may be three sets of the frame, diaphragm and aperture.

BRIEF DESCRIPTION OF THE SEVERAL VIEWS OF THE DRAWINGS

Embodiments of the invention will now be described solely by way of example and with reference to the accompanying drawings in which.

DETAILED DESCRIPTION OF THE DRAWINGS

Figure 1:
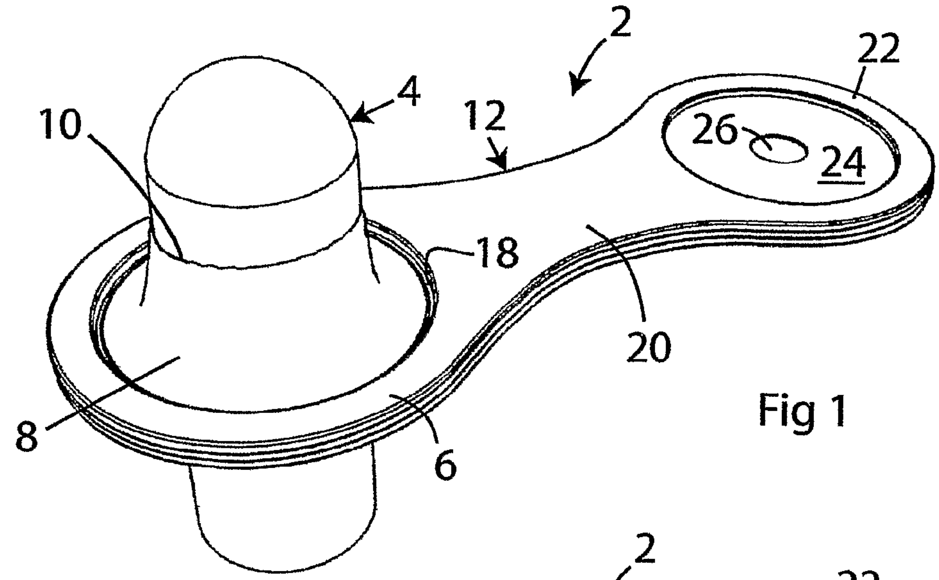
FIGS. 1, 2 and 3 show first apparatus of the invention in use.

Referring to FIGS. 1-4, there is shown apparatus 2 for receiving a phallus 4. The apparatus 2 comprises a frame 6, a diaphragm 8 supported by the frame 6, and an aperture 10 in the diaphragm 8. The apparatus 2 also comprises a handle portion 12 for holding the apparatus 2 in a user's hand.

Figure 2:
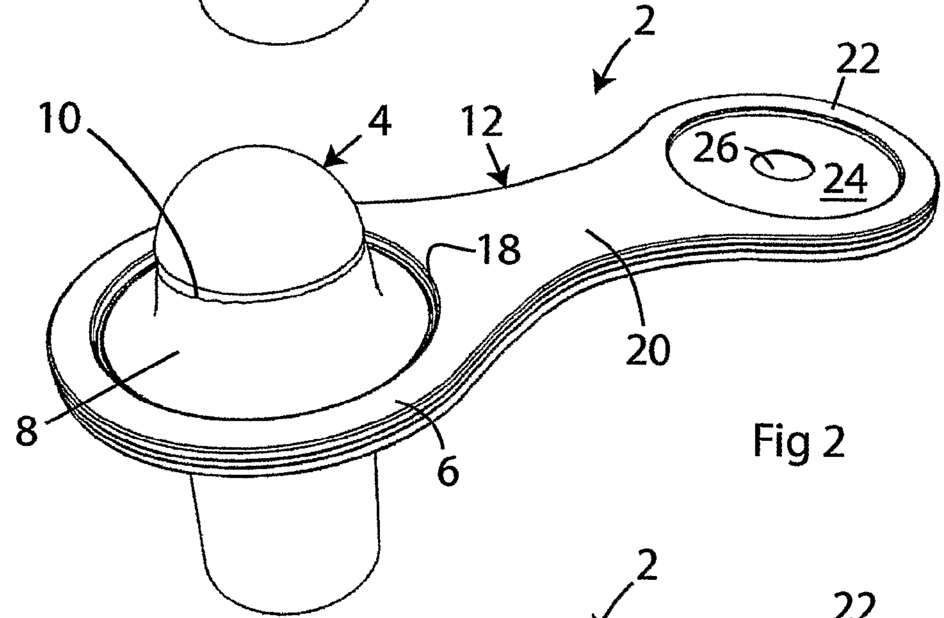
Figure 3:
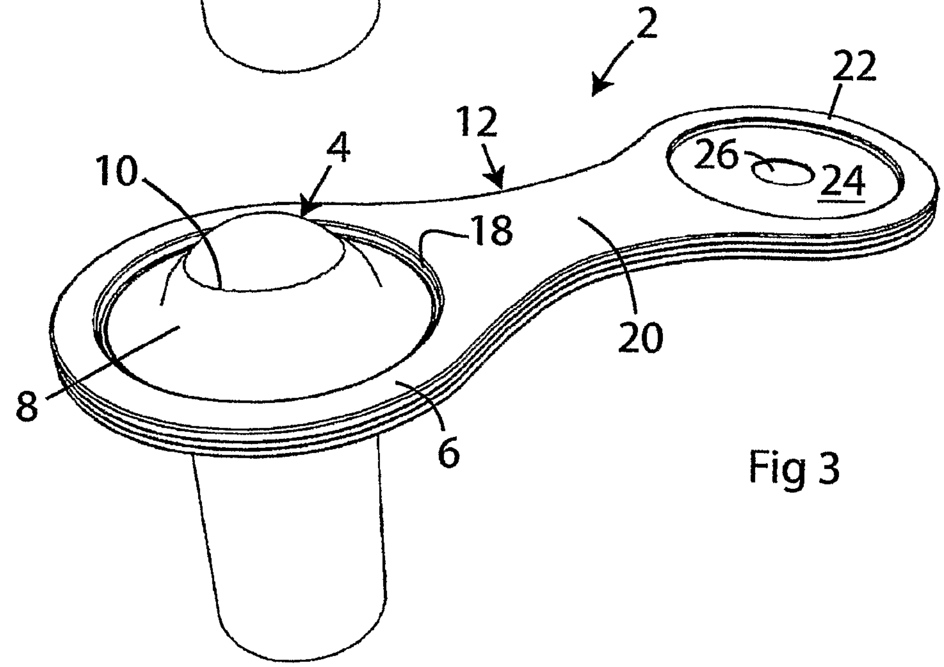

The apparatus 2 is such that the diaphragm is made of a stretchable material. The stretchable material is such that the aperture 10 is stretchable radially to enable the phallus 4 to extend through the diaphragm 8. FIG. 3 shows the phallus 4 starting to extend through the diaphragm 8. FIG. 2 shows the phallus 4 having extended a little further through the diaphragm 8, and FIG. 1 shows the phallus 4 having been inserted for a still further distance through the diaphragm 8. As can be seen from FIGS. 1, 2, and 3, the frame 6 supports the diaphragm 8 such that when the phallus 4 extends through the diaphragm 8 then the phallus 4 extends transversely through the frame 6 and projects beyond the frame 6.

As can best be seen from FIG. 1, the diaphragm 8 is stretchable transversely to extend along the phallus 4 but only for a short length which is substantially less than the length of the phallus 4. The part of the diaphragm in contact with the phallus 4 acts with a compressive force sufficient to provide the phallus 4 with sexual stimulation. As can be seen from FIG. 4, the diaphragm 8 returns to its original shape after use. As can also be seen from FIG. 4, the diaphragm 8 is substantially flat when the apparatus 2 is not in use.

The stretchable material forming the diaphragm 8 may be made of a wide variety of materials. The materials chosen may be rubber materials or plastics materials. The materials chosen may have an appropriate Shore hardness for giving the required stretchability with the required compression. As can be seen from FIGS. 1-5, the stretchable material of the diaphragm 8 is a plain material.

Figure 5:
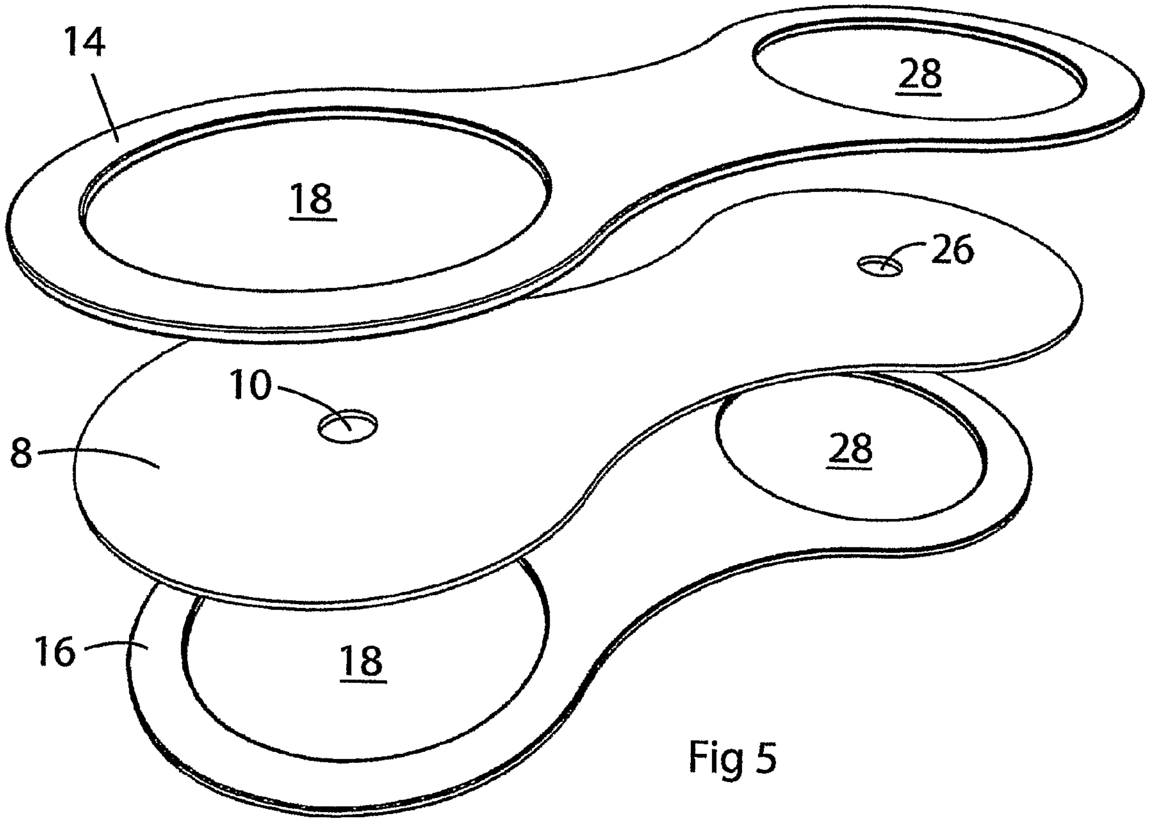
FIG. 5 is an exploded view of the apparatus as shown in FIG. 4.

As shown in FIG. 5, the frame 6 is a laminated frame. More specifically, the diaphragm 8 is held between a first layer 14 and a second layer 16 of the frame 6. The diaphragm 8 is held between the first and second layers 14, 16 by an adhesive. Any suitable and appropriate type of adhesive may be employed. The frame 6 is a rigid frame. The first and second layers 14, 16 may be made of any suitable and appropriate rigid material including plastics materials, wood, metals and solid rubber materials.

The frame 6 defines a circular area 18. The circular area 18 is filled by the diaphragm 8.

The aperture 10 is a circular aperture.

The handle portion 12 forms part of a connecting portion 20 which connects the frame 6, the diaphragm 8 and the aperture 10 to another frame 22, diaphragm 24 and aperture 26.

Figure 4:
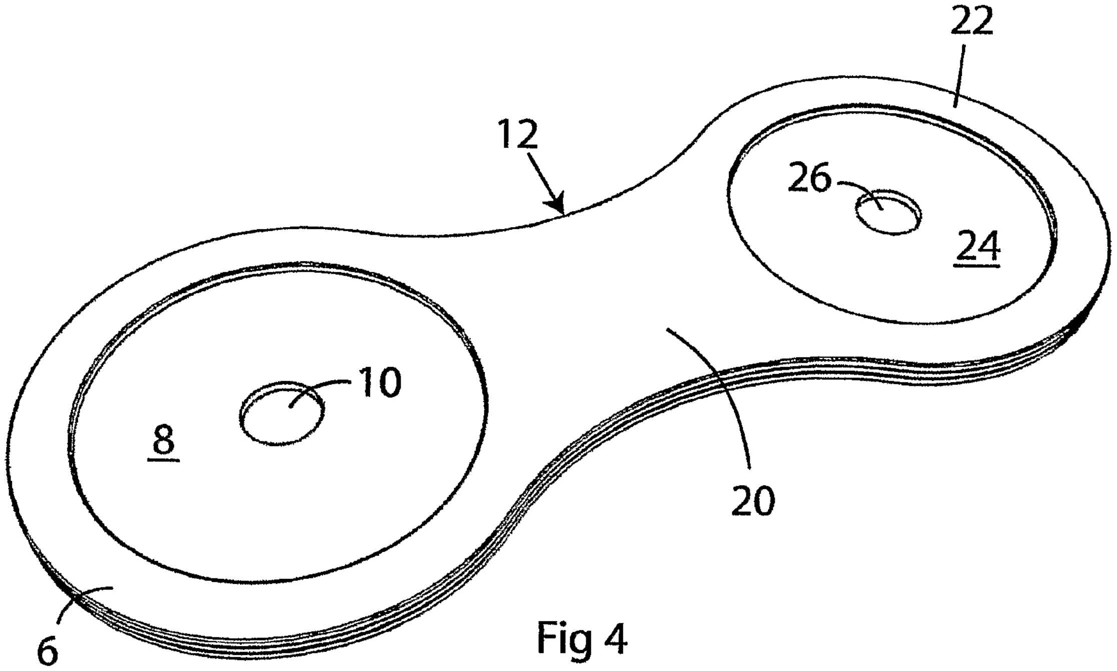
FIG. 4 is a perspective view of the apparatus shown in FIGS. 1-3 but not in use.

As shown in FIG. 4, the frame 6 and the diaphragm 8 are substantially flat when the apparatus 2 is not in use. More especially, the entire apparatus 2 is substantially flat when not in use. The flat aspect of the apparatus 2 enables the apparatus 2 to be stored and packaged in a discreet form. The diaphragm 24 may be different to the diaphragm 8 in terms of thickness and/or texture and/or Shore hardness and/or surface pattern. By such means, the diaphragm 24 may give a different sensory feeling to the phallus 4 than the diaphragm 8. Naturally, if desired, the diaphragm 24 may be the same as the diaphragm 8 but it will usually preferred that the diaphragm 24 is different to the diaphragm 8 for the purpose of giving a different sensory feel. As can best be appreciated from FIG. 5, the diaphragm 24 is formed with the diaphragm 8 and is held by the adhesive between the first and second layers 14, 16. Thus the diaphragm 24 fills a circular area 28.

Figure 6:
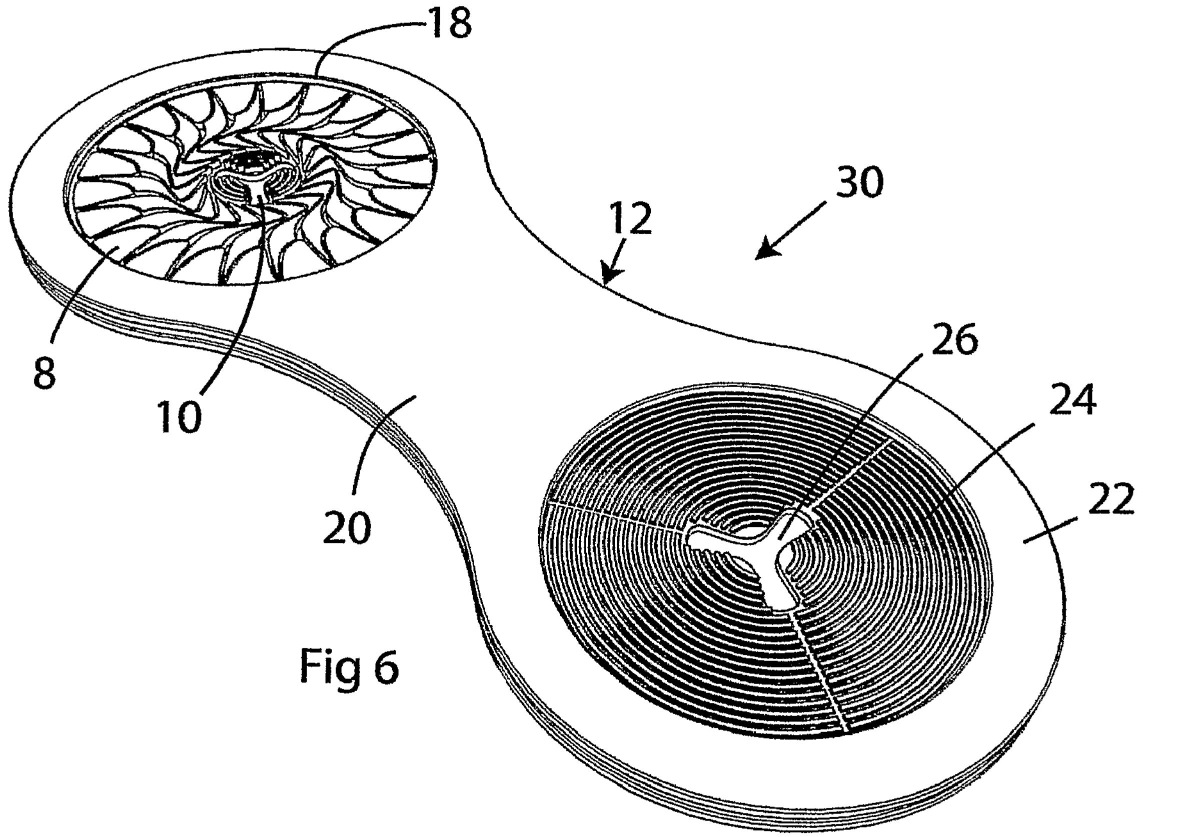
FIGS. 6-22 are perspective views of other types of apparatus of the invention.

FIG. 6 shows apparatus 30 which is like the apparatus 2. For ease of identification, similar parts have been given the same reference numerals. In the apparatus 30, it will be seen that the aperture 10 is a three-legged aperture 10 instead of a circular aperture 10 as shown in the apparatus 2. Also, the diaphragm 8 is provided with the illustrated pattern. The illustrated pattern may be provide on one or both sides of the diaphragm 8. The diaphragm 24 has a three-legged aperture 26. The diaphragm 24 has a circular ribbed pattern as shown. The circular ribbed pattern may be on one or both sides of the diaphragm 24.

Figure 7:
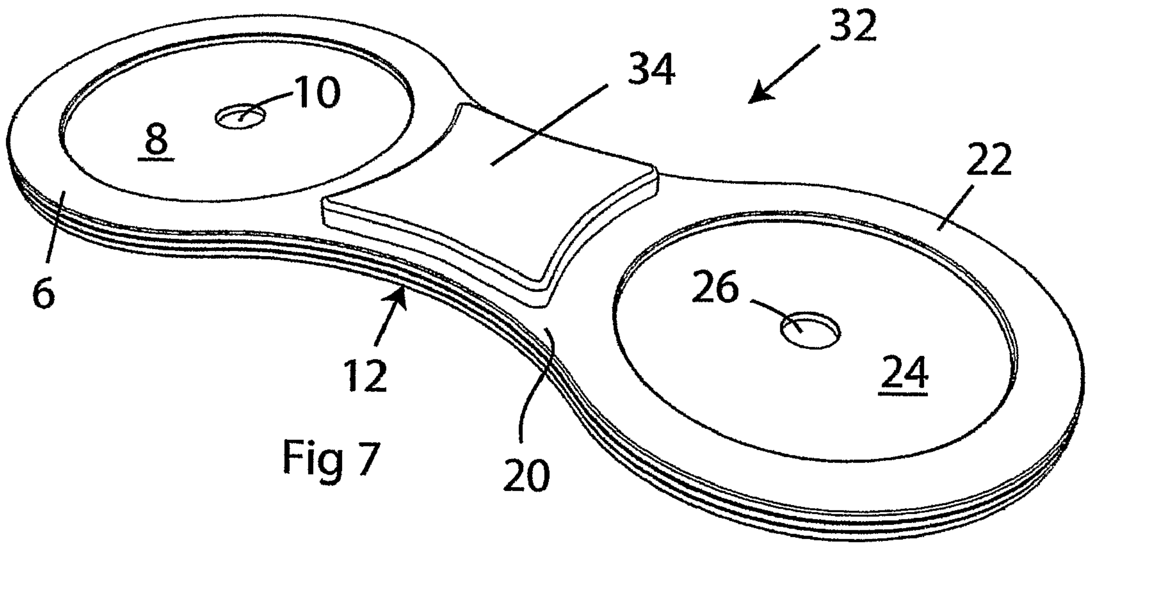

FIG. 7 shows apparatus 32 which is like the apparatus 2 except that the apparatus 32 is not entirely flat. More specifically, the handle portion 12 forms a part of the apparatus which serves a purpose in addition to being a handle portion 12. Thus, as can be seen from FIG. 7, the handle portion 12 extends into the integral connecting portion 20 for connecting to the frame 22. In addition, the handle portion 12 and the integral connecting portion 20 support a vibration unit 34.

Figure 8:
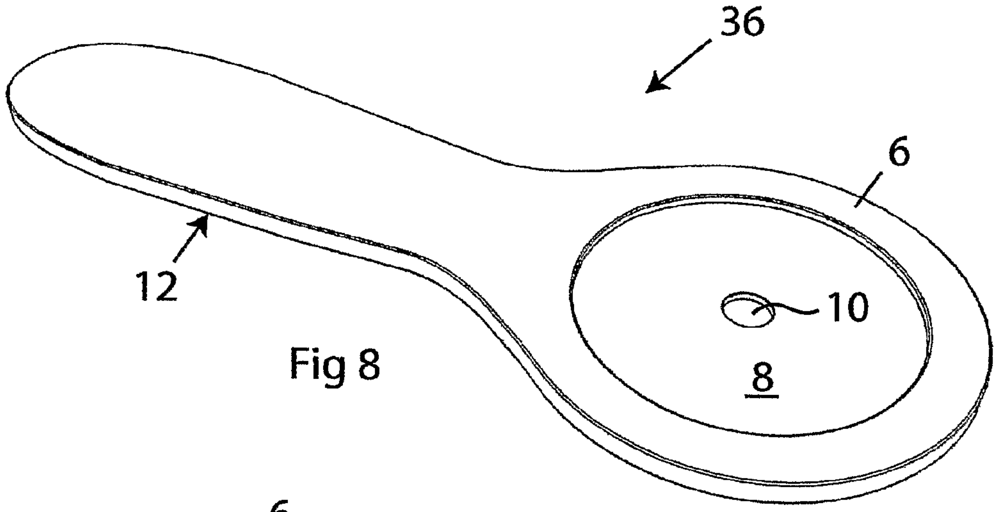

FIG. 8 shows apparatus 36 in which the handle portion 12 is a dedicated handle portion 12.

Figure 9:
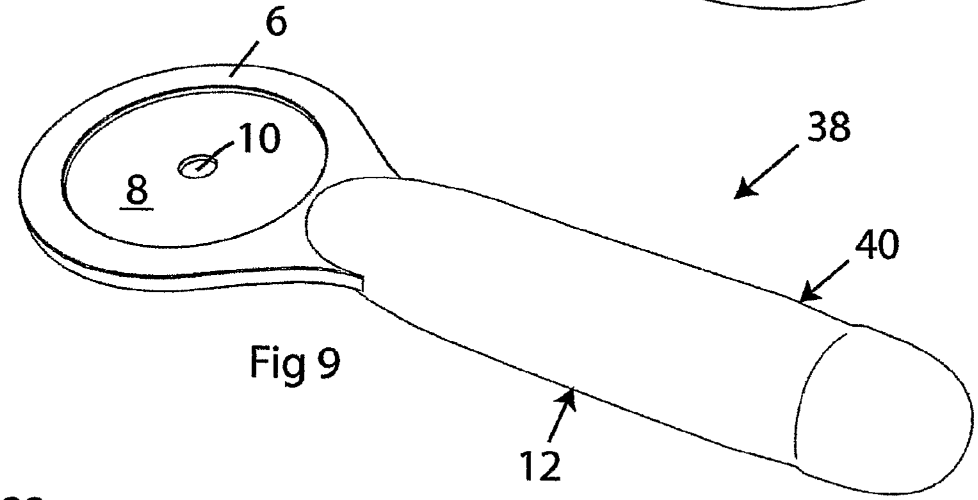

FIG. 9 shows apparatus 38 in which the handle portion 12 forms part of apparatus in the form of a vibration unit 40, and thus the handle portion 12 is connected to a part of the apparatus which serves a purpose in addition to being a simple handle portion. If desired, the handle portion 12 with the vibration unit 40 may be used as dildo.

Figure 10:
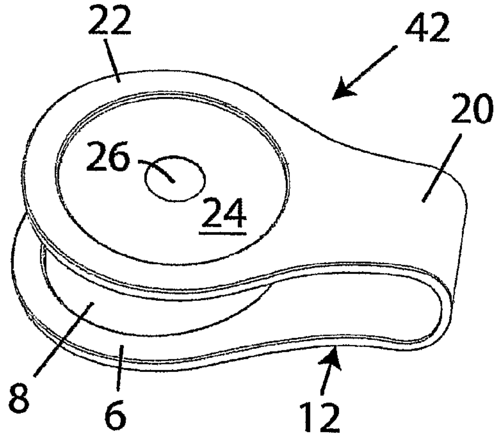

FIG. 10 shows how apparatus 42 might be initially formed like the apparatus 2 shown in FIG. 1 and then bent back on itself. In the apparatus 42, it will be seen that there are the frames 6, 22, the diaphragms 8, 24 and the apertures 10, 26. The diaphragms 8, 24 and their apertures 10, 26 are in line. The apparatus 42 may be formed flat and then bent to shape. Alternatively, the apparatus 42 may be moulded to the shape shown.

Figure 11:
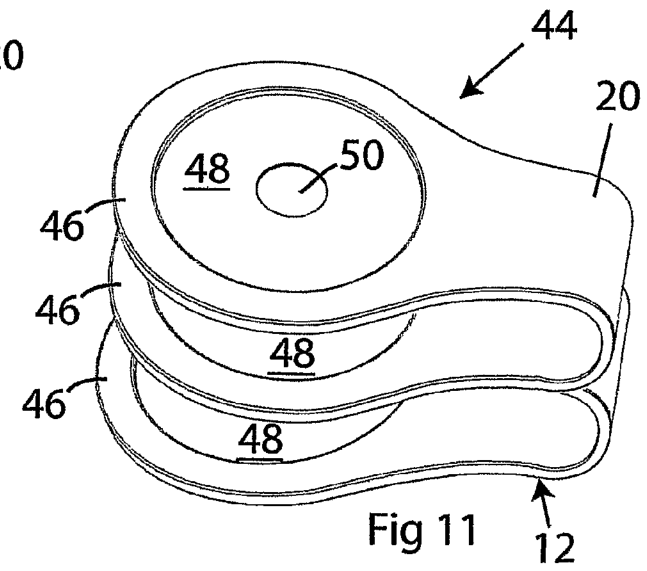

FIG. 11 shows apparatus 44 which is like the apparatus 42 except that there are three frames 46, three diaphragms 48 and three apertures 50. The diaphragms 48 and their apertures 50 are in line. The handle portion 12 is formed as shown.

Figure 12:
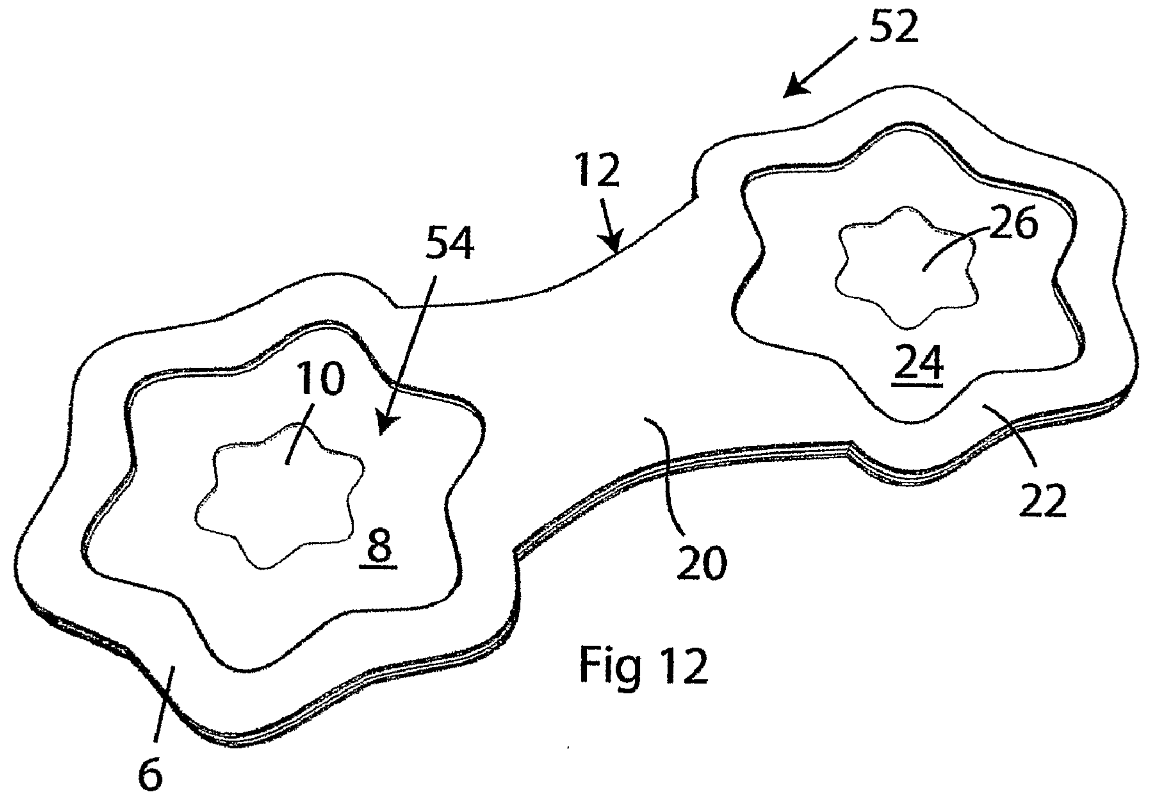

FIG. 12 shows apparatus 52 in which the apertures 10, 26 are star-shaped apertures, and in which the frames 6, 22 define star-shaped areas 54 which define the diaphragms 8, 24.

Figure 13:
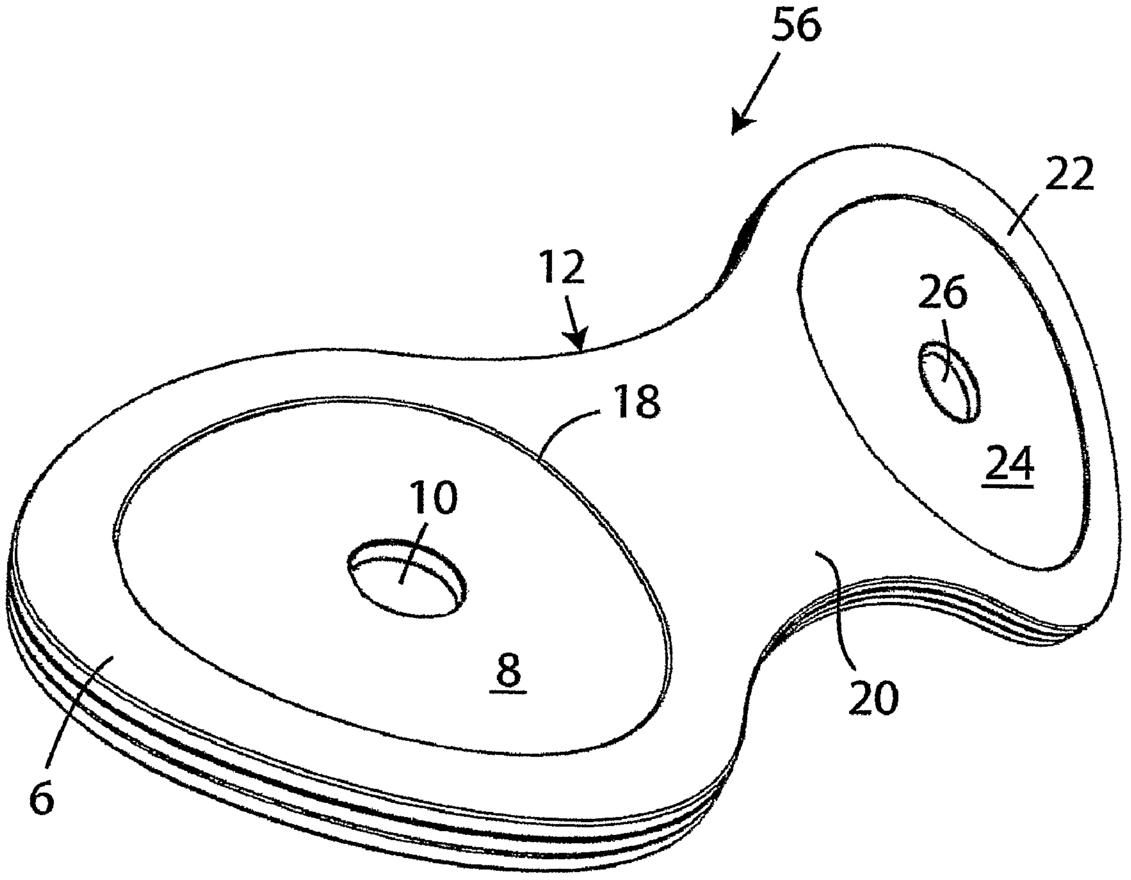

FIG. 13 shows apparatus 56 which is like the apparatus 2, but the apparatus 56 has been formed by twisting the apparatus 2 such that the apparatus 56 curves in more than one plane as shown.

Figure 14:
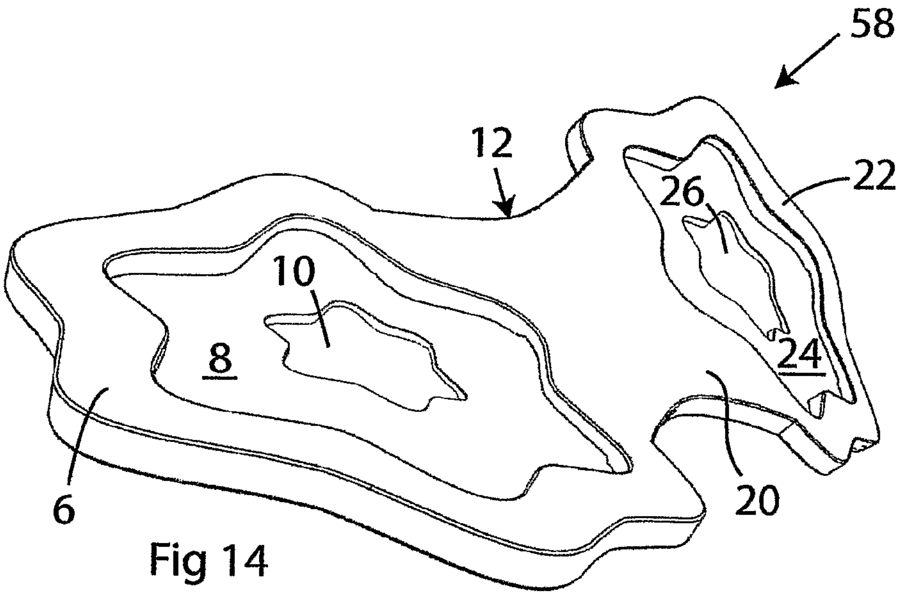

FIG. 14 shows apparatus 58 which is like the apparatus 52 shown in FIG. 12 but with the apparatus 52 being curved such that the apparatus 58 shown in FIG. 14 extends in more than one plane.

Figure 15:
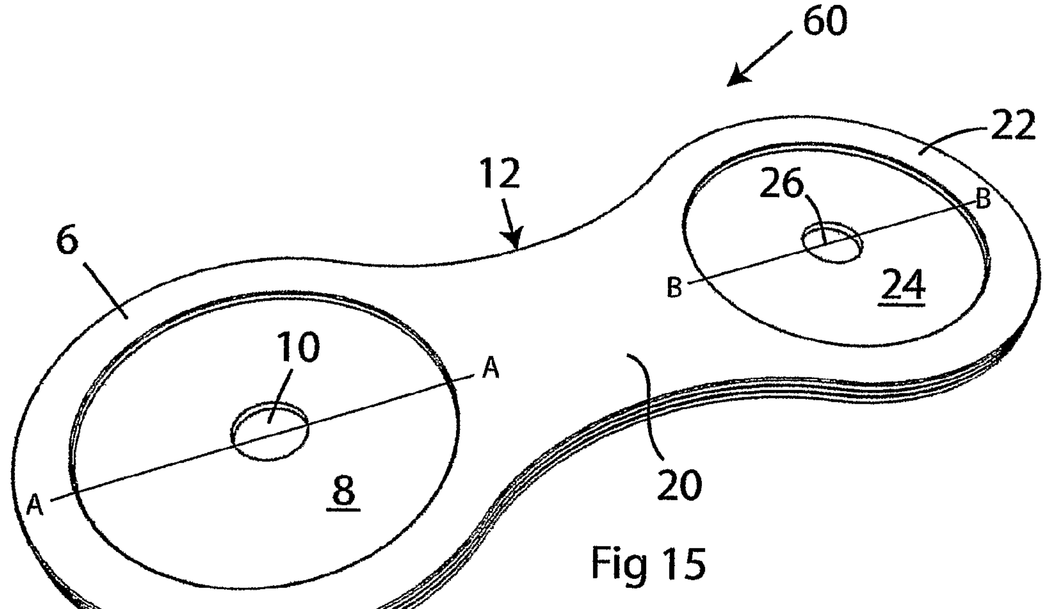
Figure 16:
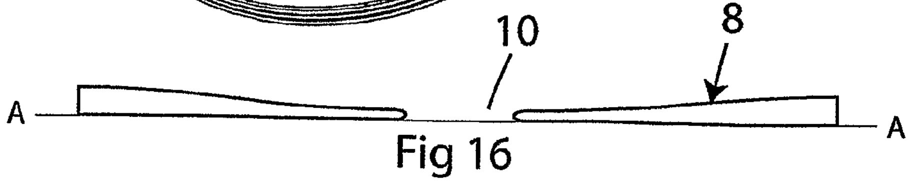
Figure 17:
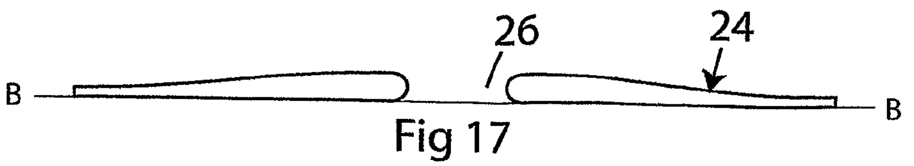

FIGS. 15, 16 and 17 show apparatus 60 which is like the apparatus 2. FIG. 16 is a section on the line A-A shown in FIG. 15, and FIG. 17 is a section on the line B-B shown in FIG. 15. In the apparatus 60, the diaphragm 8 is of an increasing thickness. The thickness of the diaphragm 8 increases in a direction away from the aperture 10 as shown in FIG. 16. The thickness of the diaphragm 24 decreases in a direction away from the aperture 26 as shown in FIG. 17.

Figure 18:
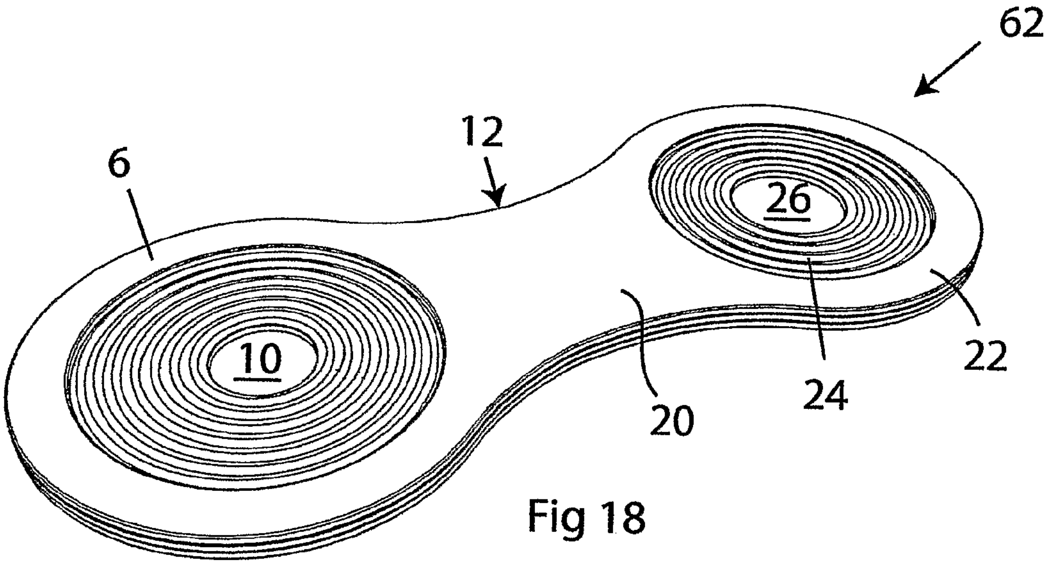
Figure 19:
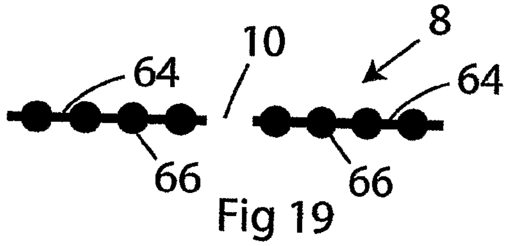

FIGS. 18 and 19 show apparatus 62 in which the diaphragm 8 is of the cross sectional formation shown in FIG. 19. Thus the diaphragm 8 has thin material parts 64 for allowing stretching, and thicker ribbed parts 66 for providing compression. In the apparatus 62, the diaphragm 24 will usually be of a different construction in terms of thickness and/or the type of ribs in order to give a different sensory feel for the phallus 4.

Figure 20:
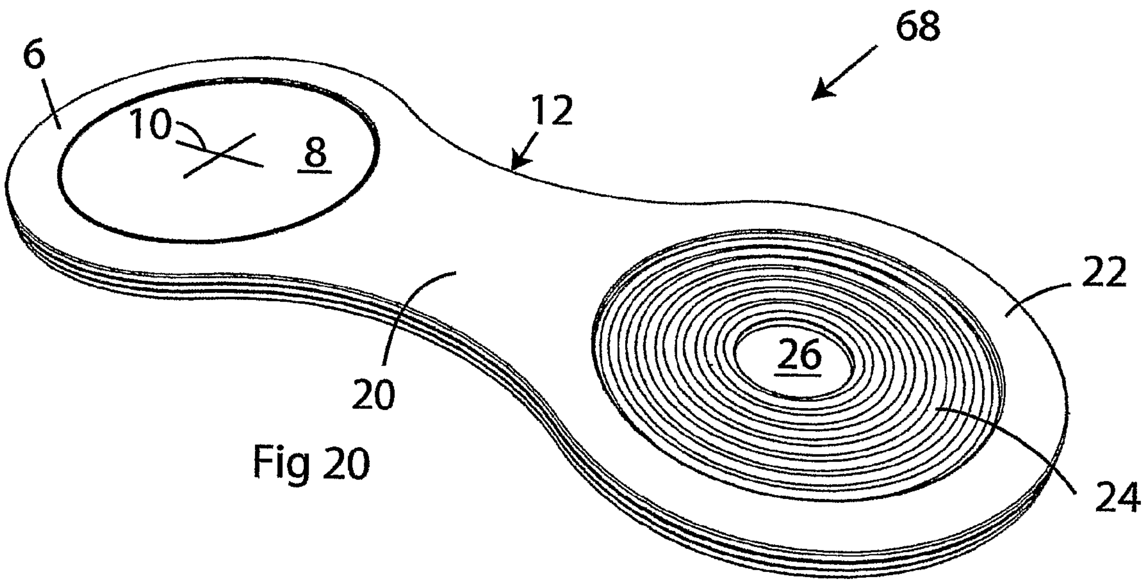

FIG. 20 shows apparatus 68 having a diaphragm 24 which gives a small concertina effect in order to allow the diaphragm 24 to stretch further as may be required. When the diaphragm 26 employs the concertina effect and when the apparatus of the invention employs two or more the diaphragms, then one or more of the diaphragms may have the concertina effect. FIG. 20 also shows the aperture 10 in the form of cross slits.

Figure 21:
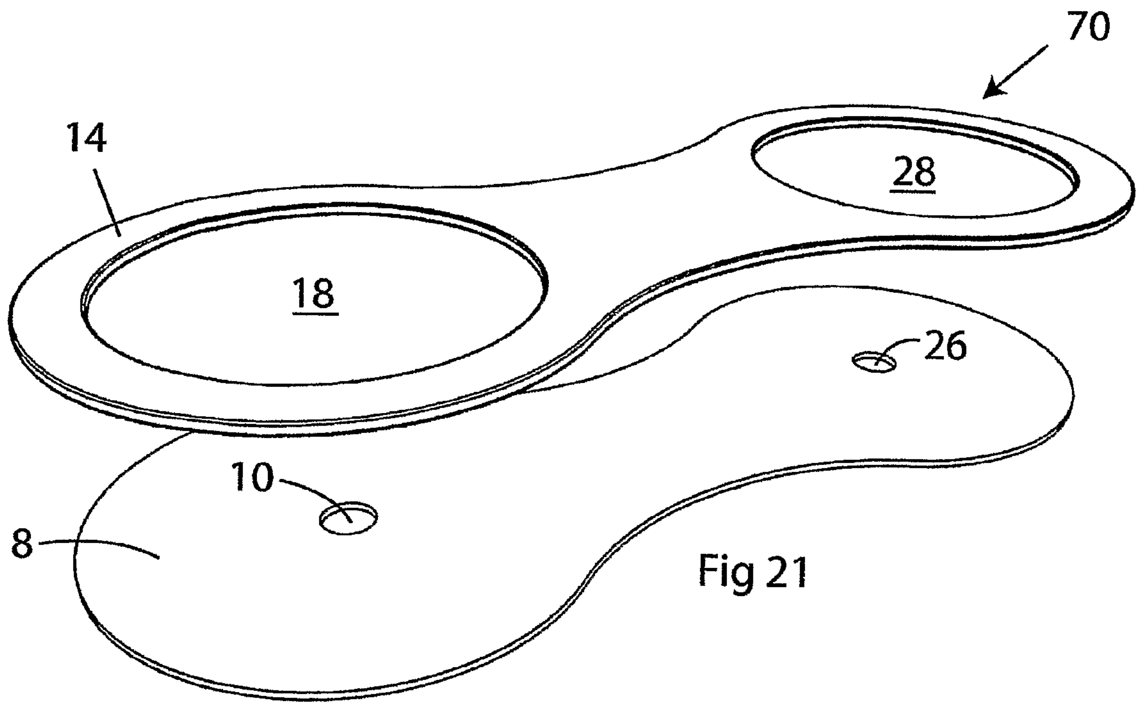

FIG. 21 shows apparatus 70 in which the frame is formed as a single layer 14. The diaphragm 8 is secured to the single layer 14 by an adhesive.

Figure 22:
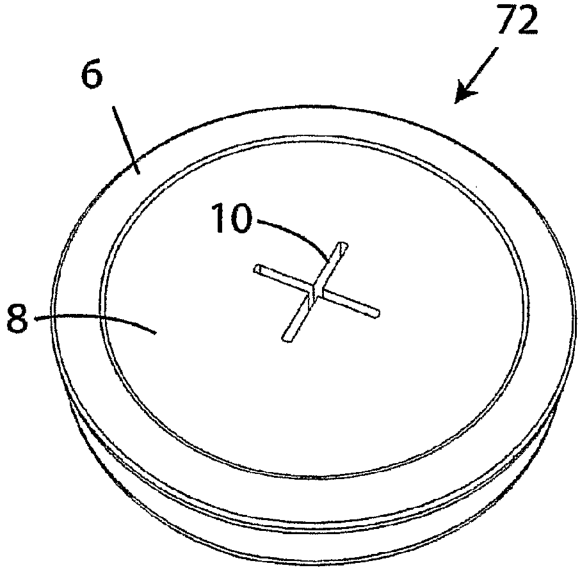

Referring now to FIG. 22, there is shown apparatus 72 in which the frame 6 is circular. The apparatus 72 does not have a handle portion. The apparatus 72 is held by the frame 6. The construction of the apparatus as shown in FIG. 22, that is without a handle portion, may be advantageous for commercial sale in vending machines. The apparatus 72 as shown in FIG. 22 may be formed with the frame as a single layer frame or a multi-layer frame as may be desired.

It is to be appreciated that the embodiments of the invention described above with reference to the accompanying drawings have been given by way of example only and that modifications may be effected. Thus, for example, the apparatus may be of different designs to those shown. Similarly, the shapes for the frames, the diaphragms and the apertures in the diaphragms may be different from those shown. Generally, the apparatus of the present invention may be made in any suitable sizes, designs and thicknesses. Graphics and/or mark branding may be applied to the handle or other parts of the apparatus of the invention.

The invention claimed is:

1. Apparatus for receiving a phallus, which apparatus comprises a frame, a diaphragm supported by the frame, and an aperture in the diaphragm, the apparatus being such that:

(i) the diaphragm is made of a stretchable material;

(ii) the diaphragm is substantially flat when not in use; and characterised in that:

(iii) the stretchable material is such that the aperture is stretchable radially to enable the phallus to extend through the diaphragm, the diaphragm is stretchable transversely to extend along the phallus but only for a short length which is substantially less than the length of the phallus, the part of the diaphragm in contact with the phallus acts with a compressible force sufficient to provide the phallus with sexual stimulation, and the diaphragm returns to its original shape after use; and (iv) the frame supports the diaphragm such that when the phallus extends through the diaphragm then the phallus extends transversely through the frame and projects beyond the frame.

2. Apparatus according to claim 1 in which the stretchable material is a rubber material or a plastics material.

3. Apparatus according claim 1 in which the stretchable material is a silicon material.

4. Apparatus according to claim 1 in which the stretchable material is plain.

5. Apparatus according to claim 1 in which the stretchable material has a raised pattern.

6. Apparatus according to claim 1 in which the frame is a laminated frame, in which the laminated frame has first and second layers, and in which the diaphragm is held between first and second layers of the laminated frame.

7. Apparatus according to claim 1 in which the diaphragm is moulded to be integral with the frame.

8. Apparatus according to claim 1 in which the frame is a rigid frame.

9. Apparatus according to claim 1 in which the aperture is selected from the group consisting of a circular aperture or a three-legged aperture.

10. Apparatus according to claim 1 and including a handle portion for holding the apparatus in a user's hand.

11. Apparatus according to claim 10 in which the handle portion forms a part of the apparatus which serves a purpose in addition to being a handle portion, and in which the handle portion forms part of a connecting portion which connects the frame, the diaphragm and the aperture to at least one other frame, diaphragm and aperture.

12. Apparatus according to claim 1 in which the frame and the diaphragm are substantially flat when the apparatus is not in use.

13. Apparatus according to claim 1 in which the entire apparatus is substantially flat when not in use.

14. Apparatus according to claim 1 in which the entire apparatus is not substantially flat when not in use, in which the handle portion forms a part of the apparatus which serves a purpose in addition to being a handle portion, and in which the part of the apparatus which serves a purpose in addition to being a handle portion is a vibration unit.

15. Apparatus according to claim 1 in which the apparatus is not substantially flat when not in use, in which there are two sets of the frame, diaphragm and aperture, and in which the apparatus is twisted such that it bends in more than one plane.

16. Apparatus according to claim 1 in which the entire apparatus is not substantially flat when not in use, in which there are at least two sets of frame, diaphragm and aperture, and in which the apparatus is formed such that the diaphragms and their apertures are in line.

* * * * *